Aug. 18, 1942. J. D. BROWNELL Plant Pat. 543
ROSE
Filed Dec. 22, 1941
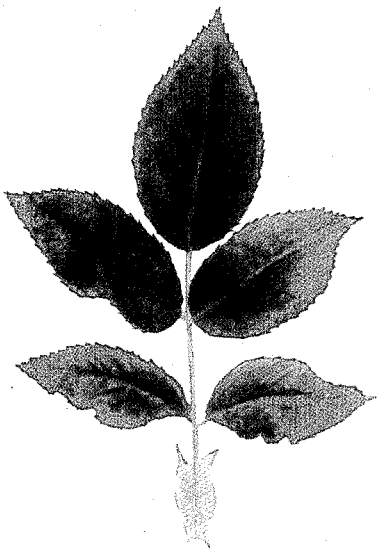
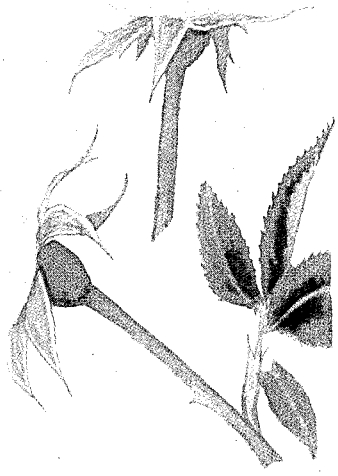
INVENTOR.
Josephine D. Brownell.

Patented Aug. 18, 1942

Plant Pat. 543

UNITED STATES PATENT OFFICE

543

ROSE

Josephine D. Brownell, Little Compton, R. I.

Application December 22, 1941, Serial No. 424,015

1 Claim. (Cl. 47—61)

My invention relates to roses and especially to a new, original and distinct variety of the class known commercially as "hybrid teas" and is a variant in that class, being a *Rosa wichuraiana* hybrid tea, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States.

The yellow to orange shades (ordinary dictionary definition) of its petals, in combination with the unique brilliance thereof and their tendency to hold these colors under exposure;

The novelty and variation within certain definite limits of the form of the bloom, its character of holding that form for a long time and the petalage of the flowers.

Its character of fragrance;

Its unusual abundance of flowers, notably after early bloom time and until frost;

The intensity of its remontant and everblooming or reblooming character;

Its character of ascending in height by recurrent branching and progressively longer stems from the base;

The character of producing many seven leafleted leaves; which character seldom has obtained on hybrid teas not having *Rosa wichuraiana* ancestry, but frequently obtains on flower stems of descendents of *Rosa wichuraiana* of the dwarf reblooming type;

And especially its characteristic of partial freedom from premature defoliation by black-spot, under certain definite conditions of exposure, without any cultural control.

In the accompanying drawing forming a part of this specification I have shown my new rose in its natural colors, that is as near as is possible to do so artificially.

My new rose is otherwise described as follows.

Essential Information

Type: Hybrid tea, *Rosa wichuraiana* hybrid, dwarf to ascending to tall to climber, for garden display, cut flower and forcing or growing under glass.

Class: Hybrid tea crossed with *Rosa wichuraiana*, further restricted by originator to include only those varieties that can survive moderately low sub-zero temperatures.

Breeding: This variety was produced and bred by me and under my direction by propagation and cross pollenation.

It came into being as a seedling grown from a seed borne on a plant of the variety "Golden Glow" a hardy climbing rose produced by me and under my direction, and the pollen parent of this new rose was the variety Condesa de Sastago.

The pollenation that fertilized the seed that grew into this new rose, as well as the pollenation that produced one of its parents was directed by me and was performed by emasculating flowers and placing thereon a bag protecting them from self and foreign pollen. These bags were later removed and the flowers were hand pollenated with a camel's hair brush and the bags immediately replaced. The date of this pollenation was July 3, 1937*. The seed was planted under my direction on December 11, 1937, and the date of the first flower was July 10, 1938.

The plant and flower seemed to be of unusual merit and I have since made and directed extensive propagations and tests thereof.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island. in the months of July and August in 1938–41 inclusive and the characters have successively reproduced, true to the original seedling.

*Flower*

Habit: It blooms out of doors in Little Compton, beginning about three days prior to the average beginning time of commercial hybrid teas and continues relative to growth of the plant until frost.

Flowers borne: Often one to two or three and frequently more on each stem, in the usual hybrid tea type of cluster. The pedicels and peduncles are medium in diameter and length, nearly erect, stiff, almost smooth, free from large prickles and bristles but with a few very small prickles varying to small hairs. Stems are long, diameter medium to notably stiff and rigid. The angle at which the stems seek to grow is about 15 degrees from the gravitational influence.

Quantity of bloom: Free to abundant, being cumulative in quantity from year to year as

*This and other dates herein are approximate.

the plant increases in size, notably free flowering through the summer.

Fragrance: Mild, distinctive, pleasing China tea in combination with that of *Rosa wichuraiana* under favorable environment.

Bud: Neck normal as described, opens well, being little to not at all affected by hot or wet weather or both, as to color and form, except at very high temperatures the color is less intense and the form of the petals is less recurled.

*Before the calyx breaks.*—Size is medium, form moderately pointed to ovoid, occasionally with one or more sepals having foliaceous parts extending beyond the apex of the calyx, pointed, serrate appendage on each side of some of the sepals, otherwise the sepals are usually normal and regular, tapering to lanceolate at their apex, turning back nearly perpendicular to the pedicel as the bud opens.

*Color of the bud as the calyx and petals open.*—Both sides of outer petals variable between Gold at (2) (reference to color chart, The Rose Manual 1930 by Dr. J. H. Nicolas, opposite page 256) and Canary at (1) shading at the base to Saffron at (1), and the inner petals to Nankin at (3).

Bloom: As the bud opens and the flower develop to maturity the color both sides of the petals slowly changes toward Lemon at (2) (same reference). The petals have a characteristic brilliance.

The flower is usually 3½ to 5 inches in diameter when fully open, infrequently more or less, petals average around 40 to 50, frequently some smaller petals and petaloids in the center, variable in number.

The flower opens high centered, recurled, showing stamens and pistils when fully open. The petals are variable from obovate to ovate to irregular and inner petals frequently with surfaces variously warped and crinkled and edges especially of the smaller petals frequently notably irregular. The larger petals often have one notch sometimes two and some have a small pointed apex forming a center tip. Texture is medium to thick and leathery both sides satiny; with slight almost invisible veining. The time of opening in favorable conditions is two to four days.

The petals are substantial and after about five to six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

Reproductive organs:

*Stamens.*—Quantity variable, around medium of slightly uneven lengths.

*Anthers.*—Nearly Mustard Yellow turning to Light Salmon Orange (this and references hereinafter to color are to Ridgway).

*Filaments*—Nearly Mustard Yellow.

*Pistils.*—Several of slightly uneven length, averaging around one-third inch long and numbering around sixty.

*Ovaries*—Usually all inclosed.

*Hips*—Frequently develop to ovoid to globular, color comparable with under side of leaves with variable colored overlay on the side exposed to the sun, moderately smooth; walls, thin, fleshy.

*Sepals.*—Persistent and break off easily after maturity.

*Seeds*—Variable in number.

*Plant*

Foliage: Is abundant, of compound leaves of three to five leaflets near the flower, five leaflets lower down the stems and frequently seven leaflets nearer the base. Size of leaflets medium, averaging in size about ¾ as large as the average hybrid tea leaflets. As the plants develop in size some of the leaflets develop to larger than the size described above. Form of leaflets usually ovate with apex moderately acute, base rounded frequently very slightly acute, edges notably warped to waving with serrations moderately irregular to normal and medium in size.

Distinctive characteristics of the leaflets are, brilliance of color, warped edges, and the form of leaflets being somewhat longer than normal in comparison with their width.

The color of the upper surface at the time of bloom is Medium Dark Green to Forest Green, underside Bice Green.

The petioles are medium with a few minute hairs on the upper sides or edges, not so noticeable as on most hybrid teas and small prickles on the under sides, hooked downward, all substantially the same color as the leaves, tinged and edged with a trace of Dahlia Carmine, the prickles turning lighter at maturity.

The stipules are medium from about one-half to three-quarters of an inch long, medium width about ¼ inch wide, noticeably narrowing toward the top, with tips terminating in hair points. The inner edges of these tips form an angle of about 90°. The edges have many very short minute hairs.

Stems are medium to large as the plant develops, color Bice Breen, side exposed to sun occasionally shaded with trace of Dahlia Carmine.

The prickles are nearly Dahlia Carmine to slightly variable, turning to lighter and more colorless.

Growth:—Habit is hybrid tea type of growth to ascending by branching and growth from the base, with some lateral stems that frequently bear smaller flowers than the terminal blooms.

Winter resistance:—From tests at Little Compton, Rhode Island this new rose plant compares in winter resistance with that of the subzero hybrid tea "Pink Princess."

Comparisons:—I know of no *Rosa wichuraiana* hybrid tea that compares with this new rose. Stargold open more star shaped, and is more nearly self in color. The bush of Stargold grows more upright and does not rebloom with such constancy through the growing season.

The flower is somewhat like McGreedy's Sunset, except this new rose has many more petals and opens in a more formal manner.

I claim:

The variety of hardy hybrid *Rosa wichuraiana* hybrid tea, characterized by its resistance to winter injury, its mild pleasing fragrance, with leaflets of a brilliant green with warped edges, with form and color substantially as shown and described, the flower being shades of nearly pure yellow with center deepening to light orange tones.

JOSEPHINE D. BROWNELL.